US009089640B2

(12) United States Patent
Mambrini et al.

(10) Patent No.: US 9,089,640 B2
(45) Date of Patent: Jul. 28, 2015

(54) APPARATUS AND KIT FOR ENCAPSULATING AT LEAST ONE COMPOUND FOR THERAPEUTIC AND/OR DIAGNOSTIC USE IN ERYTHROCYTES

(75) Inventors: Giovanni Mambrini, Urbino (IT); Sonja Serafini, Urbino (IT)

(73) Assignee: ERYDEL S.p.A., Urbino (IT)

( * ) Notice: Subject to any disclaimer, the term of this patent is extended or adjusted under 35 U.S.C. 154(b) by 154 days.

(21) Appl. No.: 13/642,594

(22) PCT Filed: Apr. 26, 2011

(86) PCT No.: PCT/IB2011/000891
§ 371 (c)(1),
(2), (4) Date: Jan. 4, 2013

(87) PCT Pub. No.: WO2011/135429
PCT Pub. Date: Nov. 3, 2011

(65) Prior Publication Data
US 2013/0101463 A1 Apr. 25, 2013

Related U.S. Application Data

(60) Provisional application No. 61/373,018, filed on Aug. 12, 2010.

(30) Foreign Application Priority Data

Apr. 26, 2010 (IT) .............................. BO2010A0255

(51) Int. Cl.
| *A61M 1/14* | (2006.01) |
| *A61M 1/36* | (2006.01) |
| *A61M 1/16* | (2006.01) |

(52) U.S. Cl.
CPC . *A61M 1/16* (2013.01); *A61M 1/14* (2013.01); *A61M 1/3687* (2013.01); *A61M 1/3693* (2013.01)

(58) Field of Classification Search
CPC ...... A61K 9/5068; A61K 35/18; A61L 29/06; A61L 29/16; A61M 1/14; A61M 1/16; A61M 1/34; A61M 1/36; A61M 1/3687; A61M 1/3692; A61M 1/3693; A61M 1/3696; A61M 2202/0064; A61M 2202/0429; A61M 2202/0439
USPC ................................. 604/4.01–6.16
See application file for complete search history.

(56) References Cited

U.S. PATENT DOCUMENTS 4,081,340 A  3/1978  Zimmermann et al.
(Continued)

FOREIGN PATENT DOCUMENTS

| DE | 23 26 244 | 10/1980 |
| EP | 1466968 | 1/1996 |
| EP | 1466968 | 10/2004 |

OTHER PUBLICATIONS

PCT International Search Report and Written Opinion dated Aug. 17, 2011.
Franco et al., Incorporation of Inositol Hexaphosphate Into Red Blood Cells Mediated by Dimethyl Sulfoxide, Life Sciences, 32:2763-2768, 1983.
Franco, et al., Preparation of Low-Affinity Red Cells With Dimethylsulfoxide-Mediated Inositol Hexaphosphate Incorporation: Hemoglobin and ATP Recovery Using a Continuous-Flow Method, American Journal of Hematology, 17:393-400, 1984.
(Continued)

*Primary Examiner* — Philip R Wiest
*Assistant Examiner* — Benjamin Klein
(74) *Attorney, Agent, or Firm* — McCarter & English, LLP

(57) ABSTRACT

A portable and highly automated apparatus and method for introducing at least one compound within erythrocytes; the apparatus comprises a reusable part provided with mechanical elements such as pumps and valves and electronic units such as a control unit; the apparatus also comprises a disposable part, which is adapted to come into contact with the sample containing the erythrocytes and is provided with a system of tubes made of deformable material, a plurality of reservoirs and one or more filters; the apparatus allows a further concentration of the erythrocytes after they have been treated; the apparatus allows to introduce the compound in the erythrocytes in a virtually totally automated manner.

21 Claims, 10 Drawing Sheets

(56) References Cited

U.S. PATENT DOCUMENTS

| | | | |
|---|---|---|---|
| 4,224,313 A | | 9/1980 | Zimmermann et al. |
| 4,420,559 A | | 12/1983 | Zimmermann |
| 4,478,824 A | | 10/1984 | Franco et al. |
| 4,652,449 A | | 3/1987 | Ropars et al. |
| 4,931,276 A | | 6/1990 | Franco et al. |
| 5,589,389 A | * | 12/1996 | Pages et al. ............... 435/306.1 |
| 5,612,207 A | * | 3/1997 | Nicolau et al. ............. 435/173.6 |
| 6,139,836 A | * | 10/2000 | Magnani et al. ........... 424/93.73 |
| 2010/0280430 A1 | * | 11/2010 | Caleffi et al. ............... 604/5.01 |

OTHER PUBLICATIONS

Heubsch et al., Journal of Cellular Physiology, 122:266-272, 1985 Abstract only.

Franco, et al., Effect of Inositol Hexaphosphate on the Transient Behavior of Red Cells Following a DMSO-Induced Osmotic Pulse, Journal of Cellular Physiology, 129:221-229,1986.

Talwar, et al., Erythrocytes as Carriers of Primaquine-Preparation: Characterization and Evolution; Journal of Controlled Release, 20 , 133-142, 1992.

* cited by examiner

APPARATUS AND KIT FOR ENCAPSULATING AT LEAST ONE COMPOUND FOR THERAPEUTIC AND/OR DIAGNOSTIC USE IN ERYTHROCYTES

TECHNICAL FIELD

The present invention relates to an apparatus, a kit, uses and a method for introducing at least one compound within erythrocytes.

BACKGROUND OF THE INVENTION

Many attempts have been recently focussed on the development of procedures for the targeted release of pharmaceutical agents in specific sites in a patient or to obtain a slow release of drugs in the patient. It is known that the effectiveness of a drug can increase when the appropriate target site is effectively reached by the drug, or when the drug is preferably released in the organ to be treated or in the cell to be treated. Furthermore, the toxicity of a drug can be reduced when the total amount of administered drug is minimised although maintaining its therapeutical action upon slow release of the drug. The interest in drug administration systems relates both to conventional agents, many of which are relatively simple organic molecules, and to more complex pharmacologically active agents such as peptides, proteins, enzymes, antibodies, antisense oligonucleotides, decoy oligonucleotides, cytokines, nucleic acids, and combinations thereof, etc.

A field of recent interest relates to the use of red blood cells (hereinafter designated as "erythrocytes" or "RBCs") as carriers to release therapeutical dosages of drugs in the blood circulation in low doses or at a desired site in a patient. The erythrocytes may be "loaded" with biologically active agents and by means of a process in which the cell membranes of the erythrocytes are made permeable and one or more agents are added to the erythrocytes then resealing the cell membranes. These "loaded" or "treated" erythrocytes offer several advantages as drug release systems and targeting systems as they are biodegradable, can be maintained in the circulation for long periods of time and can be targeted to cells such as for example macrophages.

Processes for the preparation of a cell suspension loaded in a physiological solution are disclosed in German patent No. 23 26 244 and in German patent applications published with No. (OS) 23 26 161 and 24 95 119, in which the cell membranes of erythrocytes are lysed by osmotic pressure and an electric field, respectively.

The paper "Erythrocytes as carriers of primaquine-preparation: characterization and evolution" (Naresh Talwar et al.; Journal of Controlled Realease, 20 (1992) 133-142) discloses the encapsulation of phosphate in erythrocytes. It is indicated that the suggested method involves the lysis of erythrocytes and that the treated erythrocytes are washed. However, it is nowhere mentioned or suggested that the concentration of the treated erythrocytes must and/or can be increased.

U.S. Pat. No. 4,224,313, (Zimmermann et al), discloses a method to prepare a mass of cells loaded in suspension in a solution increasing the permeability of the cell membrane by an externally induced osmotic pressure or an electric field or both. The material to be loaded includes a pharmaceutical agent which has the ability, when incorporated in a cell, to prematurely destroy the cell membranes, and a stabilising agent that can inhibit the reaction of the pharmaceutical agent with the cell membranes.

U.S. Pat. No. 4,478,824 (Franco et al.) discloses a method for incorporating substances within erythrocytes changing the internal osmotic pressure of RBCs by means of the action of chemical agents, such as DMSO and glycerol, which can cross the cell membrane and enter the cells by diffusion.

U.S. Pat. No. 4,652,449, (Ropars et al.), discloses a method and an apparatus to incorporate materials within erythrocytes by osmotic pressure. The method and the apparatus have been employed and tested only on large volumes of blood. This limits many applications to employing autologous blood, i.e. blood obtained from the same patient which will then receive the blood loaded with the drug.

U.S. Pat. No. 4,931,276, (Franco et al.), discloses a method for encapsulating non-ionic agents in erythrocytes. The method has a limited effectiveness when the desired agent to be incorporated is not anionic, or is anionic or polyanionic but is not present in the virtually isotonic aqueous means at a concentration sufficient to cause the required increases in the permeability of the cells without the destruction of the cells.

Heubsch et al., J. Cell. Physiol., 122:266-272 (1985), show that, in osmotically swollen cells, the double lipid layer that forms the membrane detaches from the cytoskeleton of the cell, and the cell considerably varies its size and becomes spherical. This does not occur in normal conditions.

The patent application with publication number EP1466968 discloses a method and a machine for encapsulating active substances in erythrocytes.

Reviews of methods for incorporating substances in cells are given by Franco et al. in Life Science 32:2763-2768 (1983), Am. J. Hematol. 17:393-400 (1984), e J. Cell. Physiol. 129:221-229 (1986).

Although the use of erythrocytes as drug release systems has been investigated by many, the methods and the devices which implement these methodologies have not yet been developed to the point of being applied normally in clinical practice, in diagnostics and in research.

Furthermore, the methodologies and the devices developed up to now are not sufficiently flexible as to allow to obtain erythrocytes for any kind of use in the therapeutic, diagnostic and research field. In particular, by following the procedures disclosed in the state of the art, it is often not possible to obtain a product that can actually be used in the diagnostic (or therapeutic) field.

A recent example of an apparatus for encapsulating a compound in erythrocytes is also disclosed in patent U.S. Pat. No. 6,139,836. Although this apparatus represents a considerable improvement with respect to the previous state of the art, it is relatively complex, expensive and difficult to use. In this connection, it should be noted that the operation of the apparatus of patent U.S. Pat. No. 6,139,836 requires the presence and the continuous intervention of a specialised operator which must operate the different components of the apparatus in the correct sequence. Therefore, the treatment (loading) of erythrocytes is relatively time-consuming and involves the risk of the operator making mistakes.

The known apparatuses cannot be appropriately carried. Due to the fact they cannot be carried, the procedure needs to therefore be carried out in dedicated structures and it is not possible to operate at sites which are more accessible to patients. Furthermore, the known apparatuses require the continuous intervention of specialised staff and are not always precise and/or sufficiently effective.

It is an object of the present invention to provide an apparatus, a kit, a use and a method, which allow to overcome at least partially the drawbacks of the state of the art and are at the same time easy and cost-effective to implement.

SUMMARY

According to the present invention, there are provided an apparatus, a kit, uses and a method according to the following independent claims and, preferably, according to any of the claims directly or indirectly dependent on the independent claims.

BRIEF DESCRIPTION OF THE DRAWINGS

The invention will now be described with reference to the accompanying drawings, which show non-limitative embodiments thereof, in which.

EMBODIMENTS OF THE INVENTION

Figure 1:
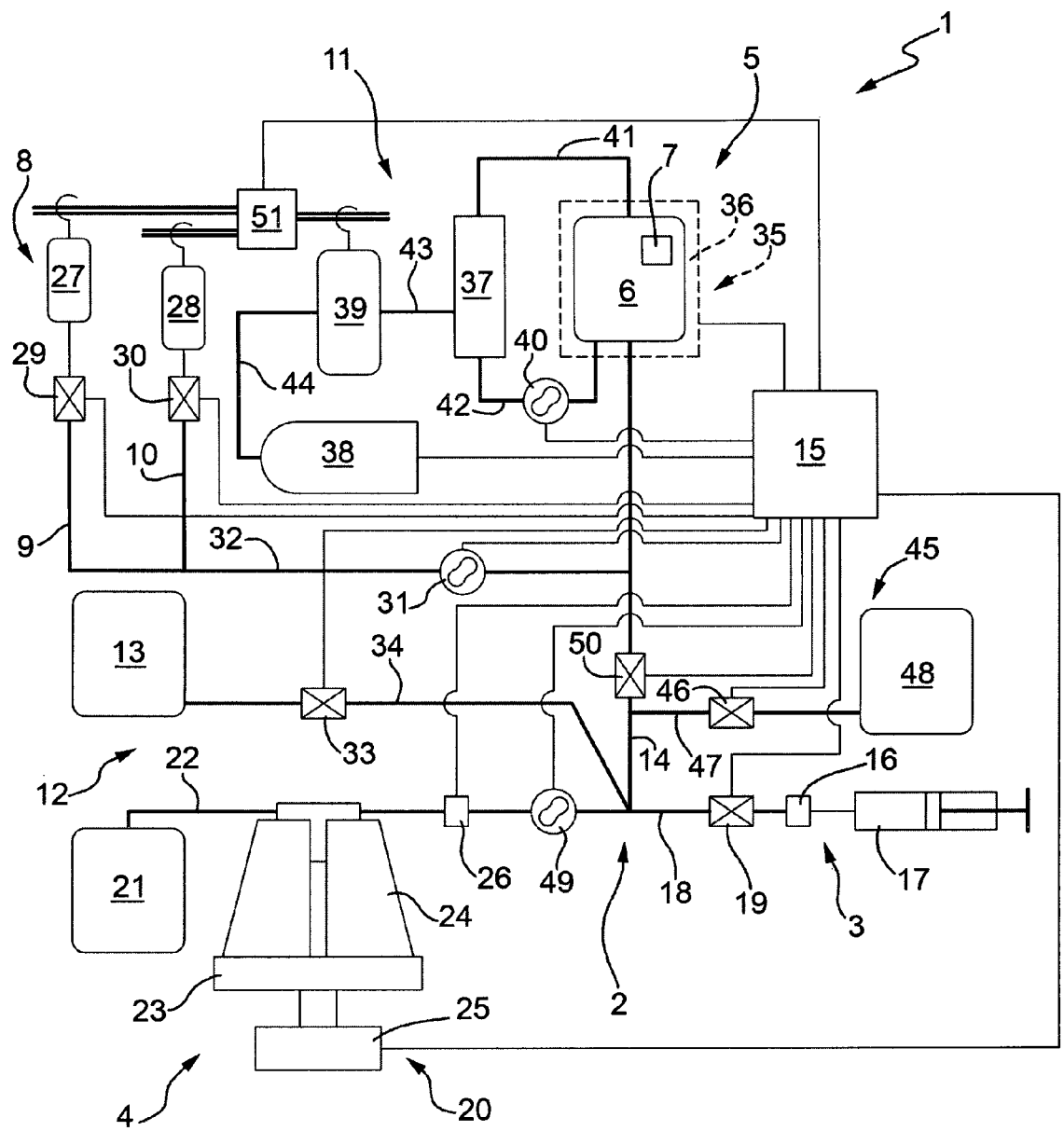
FIG. 1 is a diagram of an apparatus made according to the present invention.

According to a first aspect of the present invention, there is provided an apparatus for the introduction of at least one compound within erythrocytes.

In FIGS. 1, 5, 6, 7 and 8, numeral 1 indicates as a whole an apparatus for introducing at least one compound within erythrocytes. In particular, apparatus 1 is adapted to receive a sample of blood containing erythrocytes; receive the sample with a physiological solution so as to separate the plasma and other blood cells from erythrocytes; swell the erythrocytes and lyse them; load the compound within the erythrocytes; and close the loaded erythrocytes so as to obtain treated erythrocytes.

In particular, the physiological solution is saline and is for example an aqueous solution of 0.9% NaCl weight/volume. According to alternative embodiments, it is another solution suitable for washing blood.

More in particular, when the washed sample is contacted with a first solution, the erythrocytes swell. The swollen erythrocytes are then exposed to a second solution, that leads them to partially or totally lyse. Subsequently, the lysed or partially lysed erythrocytes are concentrated in a haemofilter. The lysed or partially lysed erythrocytes are contacted with at least one compound. Thereby, the compound is distributed both inside and outside the lysed or partially lysed erythrocytes. In other words, some of the molecules of the compound are introduced within the erythrocytes. The erythrocytes, which (at this stage of the procedure) contain the compound, are then exposed to a sealing solution. The exposure to the sealing solution induces the cell membranes to seal back, thereby encapsulating the compound within the cell. The so-called resulting "RBC carrier" or "treated erythrocyte" is then washed (with the same physiological solution as previously indicated). This is done to remove what has not been encapsulated in RBCs during the procedure.

In particular, the compounds are encapsulated using the methods of the present invention.

According to some embodiments, the compound is selected from the group consisting of: a biologically active agent, a pharmacologically active agent, nanoparticles up to 500 nm in diameter, a contrast medium for diagnostics, a substance that makes the erythrocytes identifiable with fluorescence, optical, magnetic and/or echographic detectors (and/or with any other method suitable to detect the contrast medium incorporated by the procedure in the erythrocytes). In particular, the compound is a drug, a molecular probe or a prodrug (i.e. a precursor of a biologically or pharmacologically active agent).

According to some embodiments, the compound is selected from the group consisting of: peptides, oligopeptides, polypeptides, proteins, enzymes, hormones, corticosteroids, glucocorticoids, non-steroidal anti-inflammatory agents, protease inhibitors, glutathione, cytokines, toxins, oligonucleotides and other nucleic acids and nucleoside analogs which are well known as useful therapeutic agents. These include 6-mercaptopurine (6-MP) or azathiopurine and fludarabine phosphate which are commonly used as immunosuppressive agents and inhibitory agents for the growth of malign cells, and phosphorylated azidothimidine (AZT), dideoxycitosine (ddC) and dideoxiinosine (ddI), which are useful as anti-viral agents, in particular in the treatment of AIDS.

For example, dexamethasone-21-phosphate (d-21P) can be encapsulated in RBC carriers and when the loaded RBCs are introduced in the circulatory system of a mammal, the d-21P is slowly converted to the drug dexamethasone. Since dexamethasone can cross the cell membrane of the carrier erythrocytes (while d-21P cannot), this process ensures that the mammal is provided with a constant level of the biologically active agent (in this case dexamethasone) for a certain period of time.

According to specific embodiments, the compound is selected from the group consisting of: amino acids, oligopeptides (2-10 amino acids), polypeptides (10-20 amino acids), proteins (more than 20 amino acids), hormones, corticosteroids, glucocorticoids, FANS, glutathione, cytokines, toxins, oligonucleotides (up to 20 nucleotides), polynucleotides (more than 20 nucleotides). The oligonucleotides and polynucleotides can contain one or more modified nucleotides, or nucleotide analogs. The amino acids, the oligopeptides and the polypeptides can contain one or more modified amino acids or amino acid analogs. In particular, the compound is selected from the group consisting of: amino acids, oligopeptides (2-10 amino acids), polypeptides (10-20 amino acids), proteins (more than 20 amino acids), hormones, corticosteroids, glucocorticoids, FANS, glutathione, cytokines, toxins, oligonucleotides (up to 20 nucleotides), dexamethasone sodium phosphate and betamethasone sodium phosphate, glutathione, indocyanine green (ICG).

According to some embodiments, the compound is selected from the group consisting of: active pharmacological agents, peptides, proteins, hormones, dexamethasone sodium phosphate and betamethasone sodium phosphate, glutathione, toxins, single stranded or double stranded oligonucleotides (which may include nucleotide analogues), nanoparticles with a diameter up to 500 nm, fluorescent agents, indocyanine green (ICG), other agents detectable by optical, echographic or magnetic resonance apparatuses, other contrast agents that may be used as diagnostic means of any sort and kind.

Apparatus 1 comprises a system 2 of connection channels; an introducing unit 3 to carry the sample containing the erythrocytes within apparatus 1; a separating unit 4 for separating the different components of the sample (in particular the plasma and the other cells from erythrocytes); and a combining unit 5, which comprises a reservoir 6 (in particular, a collection bag) and at which the erythrocytes and the compound are combined together so as to obtain the treated erythrocytes. It should be noted that, advantageously, apparatus 1 has a weight lower than 35 kg. Apparatus 1 is therefore easy to carry.

Apparatus 1 also comprises an inlet 7 (in particular a perforatable septum of reservoir 6) to take the compound in reservoir 6; and a feeding unit 8, which comprises a channel 9 to feed the first solution and a channel 10 to feed the second solution.

The first solution is adapted, when contacted with the erythrocytes, to swell the erythrocytes and, in particular, consists of an aqueous solution of one or more inorganic salts with an overall osmolality (i.e. adding the concentrations of all the dissolved salts) from about 100 mOsm/Kg to about 300 mOsm/Kg. More in particular, the first solution consists of 6 volumes of physiological solution (aqueous solution of NaCl at a concentration of 0.9% weight/volume) and 4.5 volumes of distilled (or deionised) water.

The second solution is adapted, when contacted with the erythrocytes, to lyse the erythrocytes and, in particular, consists of an aqueous solution of one or more inorganic salts with an overall osmolality (i.e. adding up the concentrations of all the dissolved salts) from about 10 mOsm/Kg to about 150 mOsm/Kg. More in particular, the first solution consists of 6 volumes of physiological solution (aqueous solution of NaCl at a concentration of 0.9% weight/volume) and 8 volumes of distilled (or deionised) water.

It should be noted that inlet 7 allows not only to introduce the compound within reservoir 6, but also to take the sealing solution into reservoir 6. The sealing solution is adapted, when in contact with the erythrocytes, to reseal the erythrocytes so as to at least partially encapsulate the compound. In particular, inlet 7 comprises a perforatable septum.

According to some embodiments, the sealing solution is a phosphate-inosine-glucose-pyruvate-adenine (PIGPA) solution. The PIGPA solution comprises, in particular, about 33 mM $NaH_2PO_4$; about 1.606 MKCl; about 0.194 M NaCl; about 0.1 M inosine; about 5 mM adenine; about 20 mM ATP; about 0.1 M glucose; about 0.1 M pyruvate; and about 4 mM $MgCl_2$. According to other embodiments, the sealing solution consists of an aqueous solution of one or more inorganic salts which has the same or higher osmolality than blood (i.e. the same or higher than 280 mOsm/kg). In an advantageous embodiment, about 5 ml to 7 ml of the sealing solution are used to reseal a volume of about 50-90 ml of lysed erythrocytes.

Apparatus 1 also comprises a concentrating unit 11 to concentrate the content of reservoir 6; and a collecting unit 12, which comprises a reservoir 13 (in particular a collection bag) to collect treated erythrocytes.

Channel system 2 connects (i.e. allows the passage of fluid between) introducing unit 3, separating unit 4, combining unit 5, feeding unit 8, concentrating unit 11 and collecting unit 12;

In particular, channel system 2 consists of one or more channels. More in particular, system 2 comprises a connection channel 14 between separating unit 4 and combining unit 5.

According to advantageous embodiments, in the present text, unless otherwise specified, by channel there is intended a duct which is made of elastically deformable material and, according to some embodiments, is substantially transparent in at least some parts. In particular, the duct is made of silicone, PVC or other polymers. Moreover, it can also contain textile inserts to improve the toughness.

Figure 2:
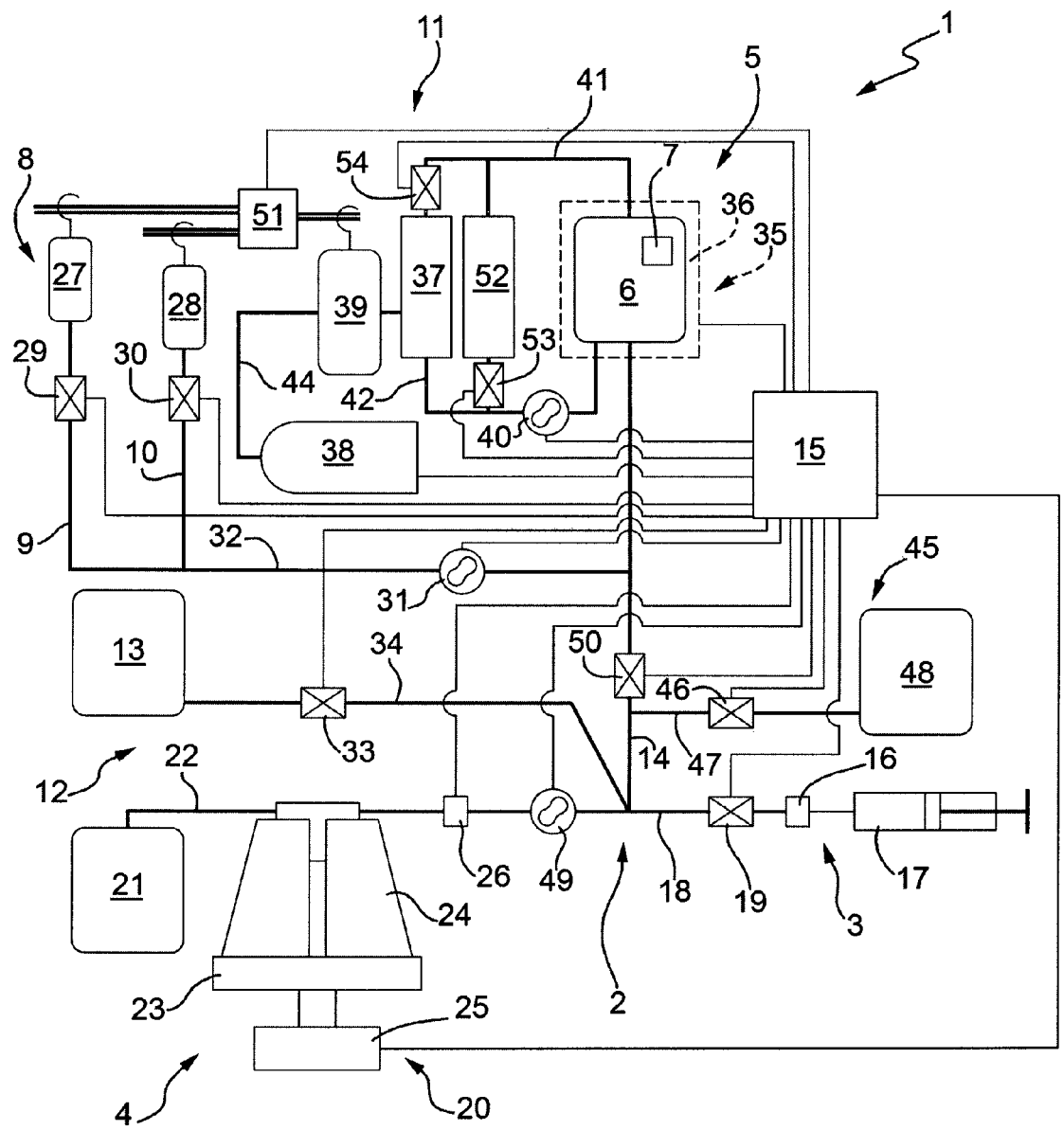
FIG. 2 is a diagram of a second embodiment of an apparatus made according to the present invention.
Figure 3:
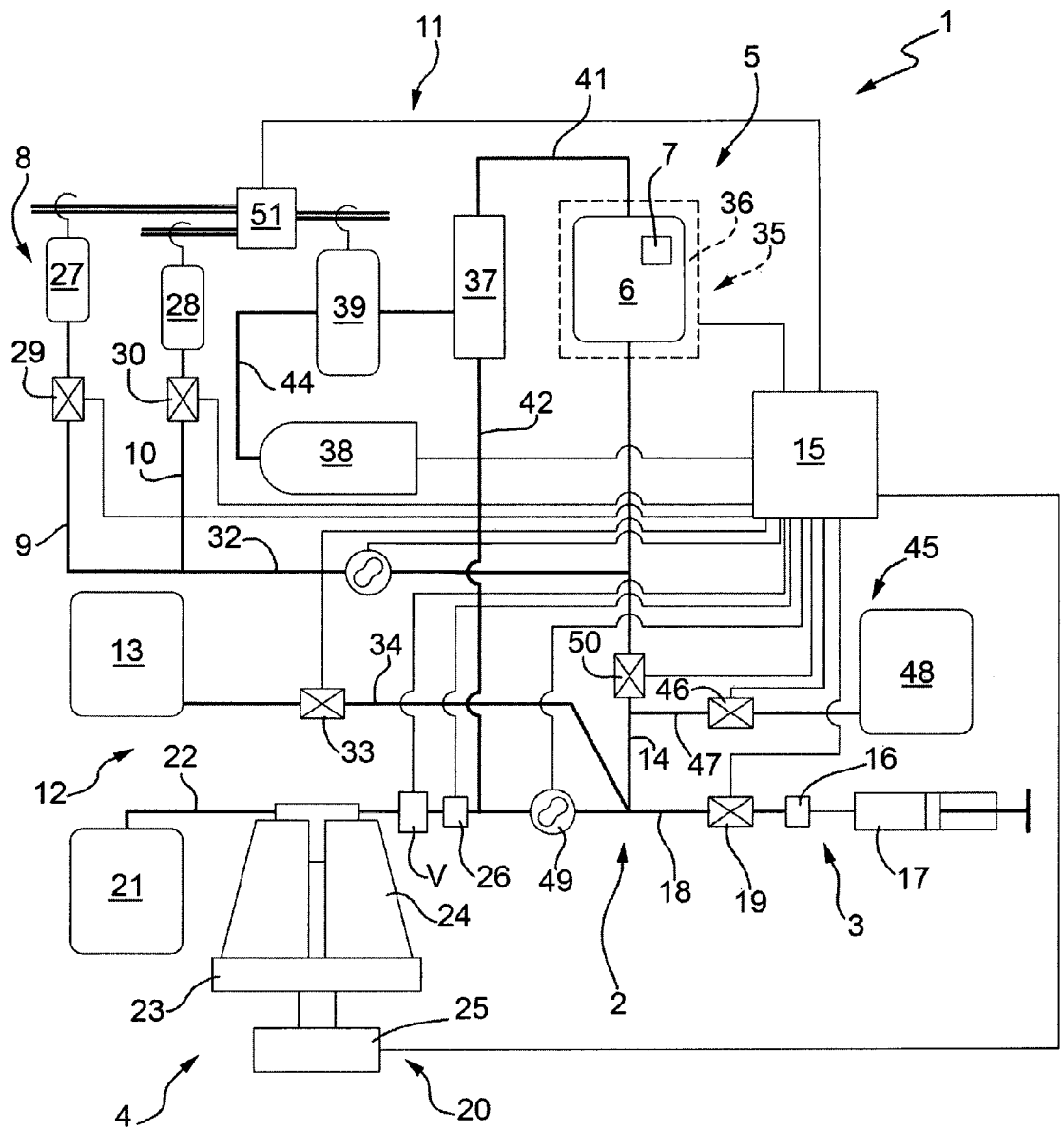
FIG. 3 is a diagram of a third embodiment of an apparatus made according to the present invention.

Apparatus 1 comprises a control unit 15, which is adapted to adjust the operation of apparatus 1. FIGS. 1-3 show the electric connections (or connections by electromagnetic waves) between the control unit and the different components of apparatus 1 by means of thin lines. Advantageously, control unit 15 comprises an electric control unit and an operator interface (HMI), which is provided for example with a display and/or a keyboard through which the operator can modify and/or display the operative parameters and the operation specifications.

According to some embodiments, introducing unit 3 comprises a perforatable septum 16 (or in any case a connection), through which the blood sample can be injected (or connected), (for example by means of a syringe 17) in channel 18 (in particular, a duct) of channel system 2. Introducing unit 3 also comprises adjusting means 19 (in particular, a valve), which are arranged along channel 18 and are adapted to adjust the flow along channel 18. According to some embodiments, channel 18 is connected to channel 14 between separating unit 4 and combining unit 5.

In particular, adjusting means 19 are adapted to totally occlude channel 18 (so as to substantially prevent the passage of fluid along channel 18) and allow the free flow of fluid through channel 18. More in particular, adjusting means 19 comprise clamp elements which are adapted to deform channel 18 so as to totally occlude the lumen of channel 18. Adjusting means 19 are operatable by control unit 15.

According to some embodiments, the separating unit 4 comprises a centrifuge assembly 20 for separating the erythrocytes and/or the treated erythrocytes from the other components of the sample. A reservoir 21 (in particular, a collection bag) is adapted to collect what has been separated from erythrocytes from separating unit 4 (in particular) centrifuge unit 20. Reservoir 21 is connected to centrifuge unit 20 by a channel (in particular a channel of system 2) 22.

According to some embodiments, centrifuge unit 20 comprises a (substantially horizontal) plate 23 adapted to rotate and a separation bowl 24 mounted on plate 23. More in particular, centrifuge group 20 comprises a motor 25 (in particular, a DC motor with sensors for detecting speed, direction and current), which is adapted to rotate plate 23 about a substantially vertical axis.

Apparatus 1 also comprises a sensor (or more sensors) 26 to detect air, partial oxygen pressure, carbon dioxide, haemoglobin, cyano haemoglobin, haematocrit, osmolarity, optical sensors for measuring absorbance/transmittance, measurement of fluorescence, magnetic resonance, acoustic wave measurement (echography) and/or other parameters upstream of separating unit 4 with respect to introducing unit 3. In particular, sensor 26 is arranged along channel 14 between channel 18 and centrifuge unit 20. Sensor 26 is connected to control unit 15 and is adapted to communicate what has been detected along channel 14 to control unit 15. According to specific embodiments, sensor 26 is adapted to detect oxygen (and/or air) upstream of separating unit 4 with respect to introducing unit 3.

In particular, sensor 26 is an ultrasound sensor (for the detection of air bubbles). Channel 14 has (at least at sensor 26) a Shore A hardness (measured according to ASTM D2240) lower than 70 (and in particular higher than 50; more specifically higher than 60). Thereby, sensor 26 can appropriately adhere to channel 14 (and therefore perform its detection activities with greater precision).

Sensor 26 is for example an AD8/AD9 ultrasound detector of Introtek®. Channel 14 is for example made of PVC XS of Sorin Group® Italia (at least in the area of sensor 26).

Sensor 26 allows to limit the presence of polluting agents within apparatus 1 and to improve the efficiency and precision of the introduction in the erythrocytes. Furthermore sensor 26 allows to obtain the exact discrimination between air and liquids during the automated process, thereby ensuring that the steps are performed correctly, and that there is no air where liquid should be and vice versa. Sensor 26 promotes the correct performance of the process in its more automated version.

Feeding unit 8 comprises a reservoir 27 (in particular a bag), which is connected to system 2 through channel 9 of system 2. Reservoir 27 contains the above mentioned first solution.

The feeding unit comprises another reservoir 28 (in particular a bag), which is connected to system 2 through channel 10 of system 2. Reservoir 28 contains the above mentioned second solution.

Introducing unit 8 comprises adjusting means 29 (in particular a valve), which are arranged along channel 9 and are adapted to adjust the flow along channel 9.

Introducing unit 8 comprises adjusting means 30 (in particular a valve), which are arranged along channel 10 and are adapted to adjust the flow along channel 10.

In particular, adjusting means 29 and 30 are adapted to totally occlude channels 9 and respectively 10 (so as to substantially avoid the passage of fluid along channels 9 and 10, respectively) and allow the fluid to freely flow through channels 9 and 10, respectively. More in particular, adjusting means 29 and 30 comprise corresponding clamp elements which are adapted to deform channels 9 and respectively 10 so as to totally occlude the lumen. Adjusting means 29 and 30 are operatable (independently of one another) by control unit 15.

Feeding unit 8 also comprises pumping means 31, which are adapted to move the first and/or second solution towards the combining unit 5 (or separating unit 4). In particular, pumping means 31 are arranged along a channel 32 (of system 2) to move the first and/or the second solution through channel 32. Channel 32 connects channels 9 and 10 to channel 14.

According to some embodiments, pumping means 31 comprise a peristaltic pump. More in particular, pumping means 31 comprise a rotor, on which one or more rollers are mounted, which deform (throttle) channel 32 repeatedly moving along a segment of channel 32.

Advantageously, collecting unit 12 comprises adjusting means 33, which are operatable by control unit 15 to adjust the flow towards reservoir 13 from system 2. In particular, adjusting means 33 are arranged along a channel 34 (of system 2), which is connected to reservoir 13.

Adjusting means 33 are structurally substantially identical to adjusting means 29 and 30 and operate on channel 86.36 cm a substantially identical way as adjusting means 29 and 30 on channels 9 and 10.

Advantageously, combining unit 5 comprises a mixing device 35 operatable by control unit 15 to move reservoir 6 so as to mix the content thereof. In particular, combining unit 5 comprises a support plate 36 to house reservoir 6; and an actuator (of the known type and not shown) to move (i.e. basculate) plate 36 and therefore mix the content of reservoir 6.

The above mentioned actuator comprises a stepper motor and 4 position sensors to control the horizontal position of plate 36, the oscillation by an angle up to +/−30° and the maintenance of an angle up to 45° (this more inclined position is taken during the emptying of reservoir 6).

Advantageously, combining unit 5 also comprises a heating element (of the known type and not shown—for example an electric resistance) controllable by control unit 15 to heat the content of reservoir 6. The operation of the heating element is controlled by temperature probes of the known type and not shown to control the operation thereof by feedback by means of control unit 15.

Advantageously, combining unit 5 also comprises an element that continuously measures the weight (of the known type and not shown—for example a loading cell) controllable by control unit 15 to measure the weight (or volume) contained in reservoir 6.

According to some embodiments, concentrating unit 11 comprises a filter 37 (in particular a haemofilter or dialysis filter) to separate at least partially the erythrocytes treated by a liquid (in particular, an aqueous solution such as for example the first and the second solution, the sealing solution and/or a physiological solution).

Concentrating unit 11 comprises an aspirator 38 (in particular, a vacuum pump that can also operate the other way around as a compressor in particular solutions of the present invention, which are not disclosed herein), which is controlled by the control unit 15 and is adapted to suck at least part of the liquid through filter 37. Aspirator 38 is controlled by one or more pressure sensors of the known type (not shown herein).

According to some embodiments of the present invention, aspirator 38 can introduce air within the channel system 2, to test the hydraulic sealing thereof and verify its correct positioning with respect to adjusting means on which it is positioned.

Concentrating unit 11 also comprises a reservoir 39 (in particular a bag or a rigid container) to collect the liquid that was passed through filter 37.

Pumping means 40 are also provided to take the content of reservoir 6 in contact with filter 37. In particular, system 2 comprises a channel 41, through which, in use, the material to be filtered and already subjected to filtration passes from reservoir 6 to filter 37 and vice versa; and, according to some embodiments, a suction channel 42, which connects filter 37 to reservoir 6 and in the area of which the pressure required for moving the fluids along channel 41 is created.

Pumping means 40 are arranged along channel 42 and advantageously comprise a peristaltic pump. More in particular, pumping means 40 comprise a rotor, on which one or more rollers are mounted, which deform (throttle) channel 42 repeatedly moving along a segment of channel 42.

Channel system 2 also comprises a channel 43, which connects filter 37 to reservoir 39; and a channel 44 that connects reservoir 39 to aspirator 38.

Apparatus 1 also comprises another feeding unit 45 to feed a third solution (in particular, a physiological solution). In particular, feeding unit 45 comprises adjusting means 46, which are operatable by control unit 15 to adjust the flow from feeding unit 45.

According to the embodiment shown, adjusting means 46 are arranged along a channel 47 (of system 2). Adjusting means 46 are structurally substantially identical to adjusting means 29 and 30 and operate on channel 119.38 cm a substantially identical way as adjusting means 29 and 30 on channels 9 and 10.

Advantageously, feeding unit 45 comprises a reservoir 48 (in particular, a bag), which contains the physiological solution, and is connected to channel system 2, in particular, through channel 47.

Apparatus 1 also comprises pumping means 49, which are operatable by control unit 15 and are adapted to move fluids at least between the introduction, separation, combination and collecting units 3, 4, 5 and 12. Advantageously, pumping means 49 are adapted to move fluids between the introduction, separation, combination, collection and feeding units 3, 4, 5, 12 and 45.

Pumping means 49 are arranged along channel 14. According to some embodiments, pumping means 49 comprise a peristaltic pump. More in particular, pumping means 49 comprise a rotor, on which one or more rollers are mounted, which deform (throttle) channel 14 repeatedly moving along a segment of channel 14.

Advantageously, introducing unit 3 and collecting unit 12 are connected to connection channel 14 between pumping means 49 and combining unit 5. Feeding unit 8 (and possibly feeding unit 45) is also connected to connection channel 14 between pumping means 49 and combining unit 5.

According to some embodiments, the apparatus also comprises adjusting means 50, which are operatable by control unit 15 and are arranged along said channel 14. In particular, adjusting means 50 are arranged between feeding unit 8 and separating unit 4.

Adjusting means 50 are structurally substantially identical to adjusting means 29 and 30 and operate on channel 14 in a substantially identical way as adjusting means 29 and 30 on channels 9 and 10.

According to some embodiments, adjusting means 50 are arranged between separating unit 4 and feeding unit 8. According to specific embodiments, adjusting means 50 are arranged between introducing unit 3 and collecting unit 12 (and possibly feeding unit 45) on one side and combining unit 5 on the other side. According to the embodiments shown, adjusting means 50 are arranged between pumping means 49 and combining unit 5.

According to some embodiments which are not shown, apparatus 1 has no adjusting means 50.

Advantageously, apparatus 1 also comprises a weighing device 51 which is adapted to detect the weight of reservoirs 27 and 28. Weighing device 51 is also adapted to detect the weight of reservoir 39. Advantageously, weighing device 51 is adapted to detect the weight of reservoir 21. According to some embodiments (not shown), weighing device 51 is adapted to detect the weight of reservoir 48.

According to some embodiments (not shown), weighing device 51 is adapted to detect the weight of introducing unit 3.

Weighing device 51 is adapted to transmit the detected data to control unit 15. In particular, control unit 15 is adapted to adjust the operation of adjusting means 29 and 30 of pumping means 31 and of aspirator 38 as a function of the weights of reservoirs 27, 28 and 39 detected by weighing devices 51.

According to some embodiments, aspirator 38 can introduce air within channel system 2 before the operator introduces syringe 17 containing the blood, to test the hydraulic sealing thereof and verify its correct positioning with respect to the adjusting means on which it is positioned.

A brief description of the operation of apparatus 1 is disclosed hereinafter starting from a time, when an operator introduces a blood sample through septum 16 by means of syringe 17 (which could also be replaced by a bag). The following description specifies, unless otherwise explicitly indicated, that the different parts of apparatus 1 are controlled by control unit 15.

During the injection of the sample, adjusting means 50, 33 and 46 are maintained closed while adjusting means 19 are maintained open and pumping means 49 move the sample towards separating unit 4. Motor 25 is operated so as to rotate plate 23 (and separation bowl 24). When the whole sample has entered in separation bowl 24, sensor 26 detects the presence of compounds (in particular oxygen) along channel 14, adjusting means 19 are closed and adjusting means 46 are opened so that the physiological solution reaches separation bowl 24.

At this point, separation bowl 24 separates the erythrocytes from the plasma and other cells, which are taken into reservoir 21.

After separation of the plasma, motor 25 is stopped and the erythrocytes are taken into reservoir 6 by operating pumping means 49 and maintaining adjusting means 19, 46 and 33 closed and adjusting means 50 open.

At this point, pumping means 49 are stopped and pumping means 31 operated so as to take the first solution into reservoir 6. During the transfer of the first solution within reservoir 6, adjusting means 30 and 50 (in particular, also adjusting means 19, 33 and 46) are maintained closed while adjusting means 29 are maintained open.

The operation of pumping means 31 (and therefore the amount of the first solution taken in the reservoir 1) is adjusted by control unit 15 on the basis of the weight (in particular, of the variation of the weight) of reservoir 27 detected by weighing device 51.

According to alternative embodiments, adjusting means 50 are maintained open so that part of the first solution reaches separation bowl 24 so as to wash separation bowl 24. In this case, the portion of the first solution that is taken in separation bowl 24 is transferred to reservoir 6 operating pumping means 49.

Once the first solution has been introduced in reservoir 6, pumping means 31 are locked and the actuator of plate 36 is operated so as to gently tilt reservoir 6. The tilting proceeds for about 5-20 minutes. Thereby, the erythrocytes are at least partially swollen.

After tilting, the content of reservoir 6 is taken into separation bowl 24 by operating pumping means 49 and maintaining adjusting means 50 open.

In separation bowl 24 (when pumping means 49 are stopped) the at least partially swollen erythrocytes are concentrated by the operation of motor 25.

After having concentrated the erythrocytes, motor 25 is stopped and pumping means 49 are activated so as to take the at least partially swollen erythrocytes back into reservoir 6.

At this point, adjusting means 50 are closed and pumping means 31 are operated again maintaining adjusting means 29 open and adjusting means 30 closed so as to take the second solution into reservoir 6.

According to alternative embodiments, adjusting means 50 are maintained open so that part of the second solution reaches separation bowl 24 so as to wash separation bowl 24. In this case, the portion of the second solution that is taken in separation bowl 24 is transferred to reservoir 6 operating pumping means 49.

The operation of pumping means 31 (and therefore the amount of the second solution taken in reservoir 1) is adjusted by control unit 15 on the basis of the weight (in particular, of the variation of the weight) of reservoir 28 detected by weighing device 51.

Once the second solution has been introduced in reservoir 6, pumping means 31 are locked and the actuator of plate 36 is operated so as to gently tilt reservoir 6. The tilting operation proceeds for about 1-30 minutes, advantageously 5-20 minutes. Thereby, the erythrocytes are at least partially lysed. During mixing of reservoir 6, adjusting means 50 are kept closed.

At this point, pumping means 40 are operated to take the content of reservoir 6 to filter 37 through channel 41. When the erythrocytes have reached filter 37, pumping means 40 are stopped and aspirator 38 is then operated so as to concentrate the at least partially lysed erythrocytes. The concentration is performed until an appropriate amount of fluid is recovered in reservoir 39. The correct content of reservoir 39 is measured by detecting the variation of the weight of reservoir 39 by means of weighing device 51.

In other words, the operation of aspirator 38 (and therefore the amount of the aqueous solution taken into reservoir 39) is adjusted by control unit 15 on the basis of the weight (in particular, of the variation of the weight) of reservoir 39 detected by weighing device 51.

After the at least partially lysed erythrocytes have been concentrated, aspirator 38 is stopped and pumping means 40 are operated so as to take the erythrocytes back into reservoir 6.

The operator therefore injects the compound through inlet 7 and subsequently plate 36 is tilted for about 1-45 minutes.

After tilting, the operator injects the sealing solution into reservoir 6 through inlet 7. At this point, the reservoir is tilted for about 10-40 minutes at a temperature of about 25-40° C. so as to obtain the at least partially treated erythrocytes.

The content of reservoir 6 is therefore transferred to reservoir 13 by operating pumping means 49, maintaining adjusting means 50 and 33 open and adjusting means 46 and 19 closed (in particular also adjusting means 29 and 30).

According to an embodiment (not shown), apparatus 1 has no pumping means 31. In this case, the first and the second solution are moved in virtue of pumping means 49 and appropriately control the above mentioned adjusting means.

Figure 8:
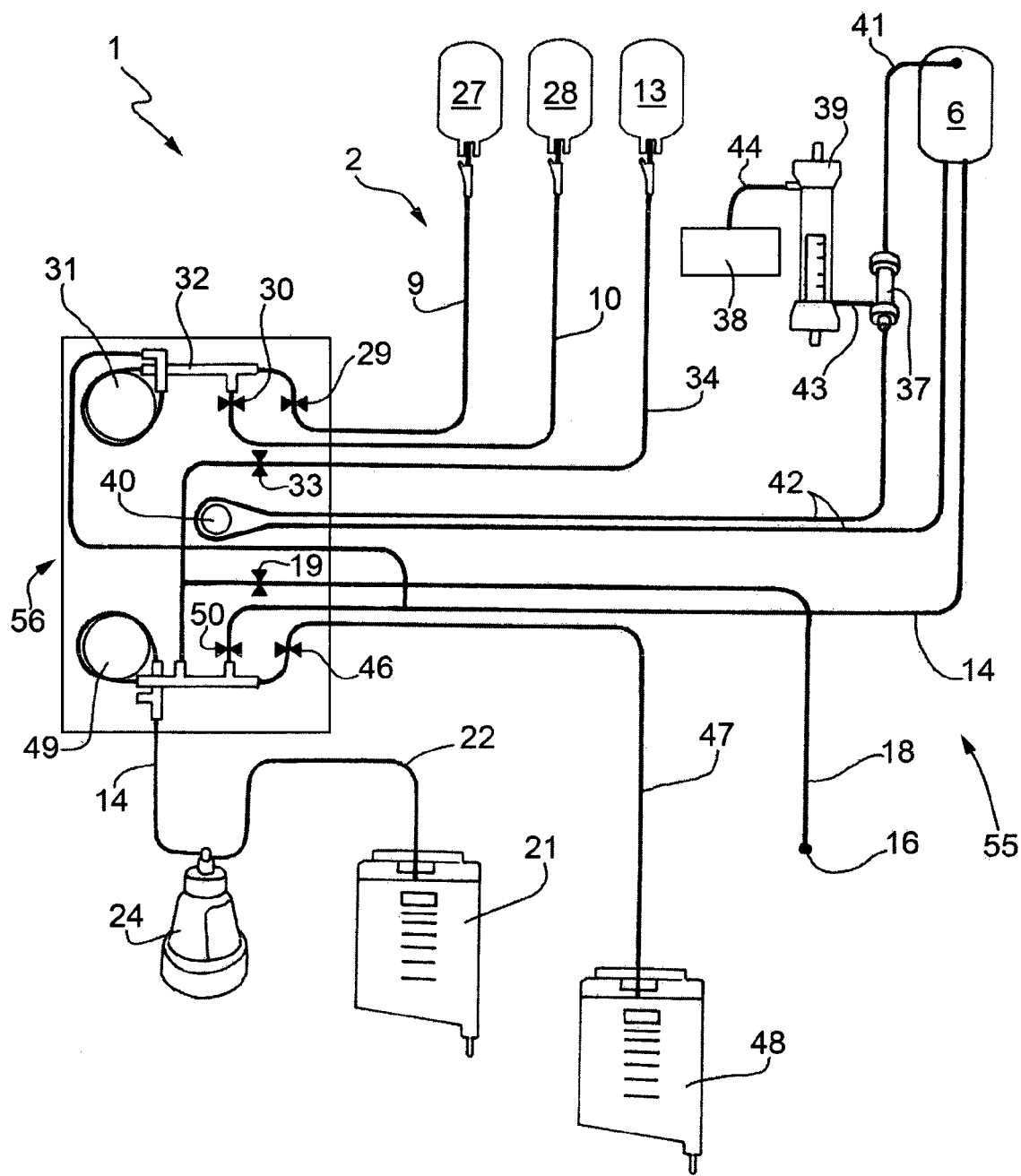
FIG. 8 diagrammatically shows some parts of the apparatus of FIG. 1.

FIG. 3 shows a variant of apparatus 1 that differs from apparatus 1 of FIGS. 1 and 8 only because apparatus 1 has no pumping means 40, comprises adjusting means V (in particular, arranged along channel 14 between pumping means 49 and separating unit 4) and channel 42 is connected to connection channel 14 (in particular, between pumping means 49 and separating unit 4). In this case, the transfer of the content of reservoir 6 to filter 37 is performed by operating pumping means 49 and maintaining adjusting means 50 open and adjusting means V closed.

Adjusting means V are structurally substantially identical to adjusting means 29 and 30 and operate on channel 14 in a substantially identical way as adjusting means 29 and 30 on channels 9 and 10.

FIG. 2 shows a variant of apparatus 1 that allows to concentrate the treated erythrocytes before the transfer to reservoir 13. The variant of FIG. 2 differs from the variant of FIGS. 1 and 8 exclusively by comprising a further filter 52 (in particular a haemofilter or dialysing filter) and adjusting means 53 and 54 (operatable by control unit 15). Filter 52 and adjusting means 53 are mounted between channels 41 and 42 and are adapted to concentrate the at least partially treated (and washed) erythrocytes before the erythrocytes are transferred to reservoir 13. Adjusting means 54 are arranged along channel 41 between reservoir 6 and filter 37.

Adjusting means 53 and 54 are structurally substantially identical to adjusting means 29 and 30 and operate in a substantially identical way as adjusting means 29 and 30.

In use, in particular, after the at least partially treated erythrocytes have been obtained in reservoir 6, the content of reservoir 6 is taken to filter 52 by operating pumping means 40 and maintaining adjusting means 54 closed and adjusting means 53 open. When the erythrocytes have reached filter 52, pumping means 40 are stopped and aspirator 38 is operated so as to concentrate the at least partially treated erythrocytes. The concentration is performed until an appropriate amount of fluid is recovered in reservoir 39. After the at least partially treated erythrocytes have been concentrated, aspirator 38 is stopped and pumping means 40 are operated so as to take the erythrocytes back into reservoir 6.

Advantageously, apparatus 1 comprises a disposable device 55 (see in particular FIG. 9) which comprises all the parts of the apparatus which come into direct contact with the erythrocytes. In particular, device 55 comprises channel system 2, reservoirs 6 and 13 and inlet 7. According to some embodiments, (for example that shown in FIG. 9) device 55 also comprises the filter/s 37 and/or 52, reservoirs 27, 28 and 48 and separation bowl 24. Advantageously, device 55 also comprises reservoirs 21 and 39.

It should be noted that device 55 comprises the only parts that are in contact or could potentially come in contact with the blood. The fact that device 55 is disposable considerably simplifies the use of apparatus 1 and improves the safety and speed of use.

Apparatus 1 also comprises a reusable device 56, which is adapted to serve as a support on which device 55 is mounted. Some details of an embodiment of device 56 are shown in FIG. 4.

Device 56 comprises pumping means 49 and adjusting means 29, 30 and 33. According to some embodiments, (as that shown in FIG. 4) device 56 also comprises pumping means 49, adjusting means 19 and 46, the motor to rotate plate 36 (and, advantageously, plate 36). Device 56 advantageously also comprises aspirator 38 (and advantageously sensor 26 and weighing device 51). According to specific embodiments, device 56 also comprises adjusting means 50. In particular, device 56 also comprises pumping means 31 and/or 40.

Figure 4:
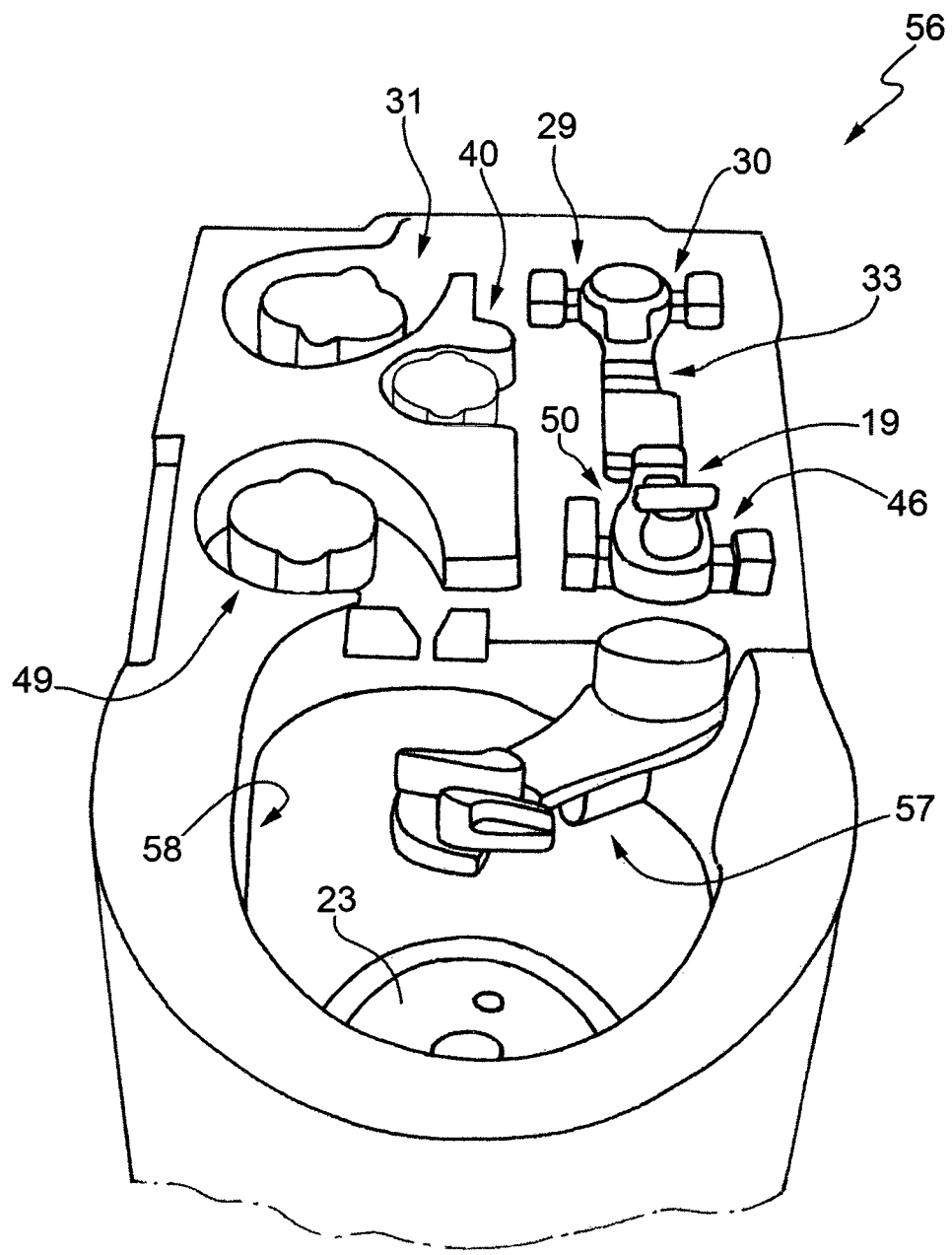
FIG. 4 is a partial perspective view with details removed for clarity of a reusable device of apparatus of FIG. 1.
Figure 5:
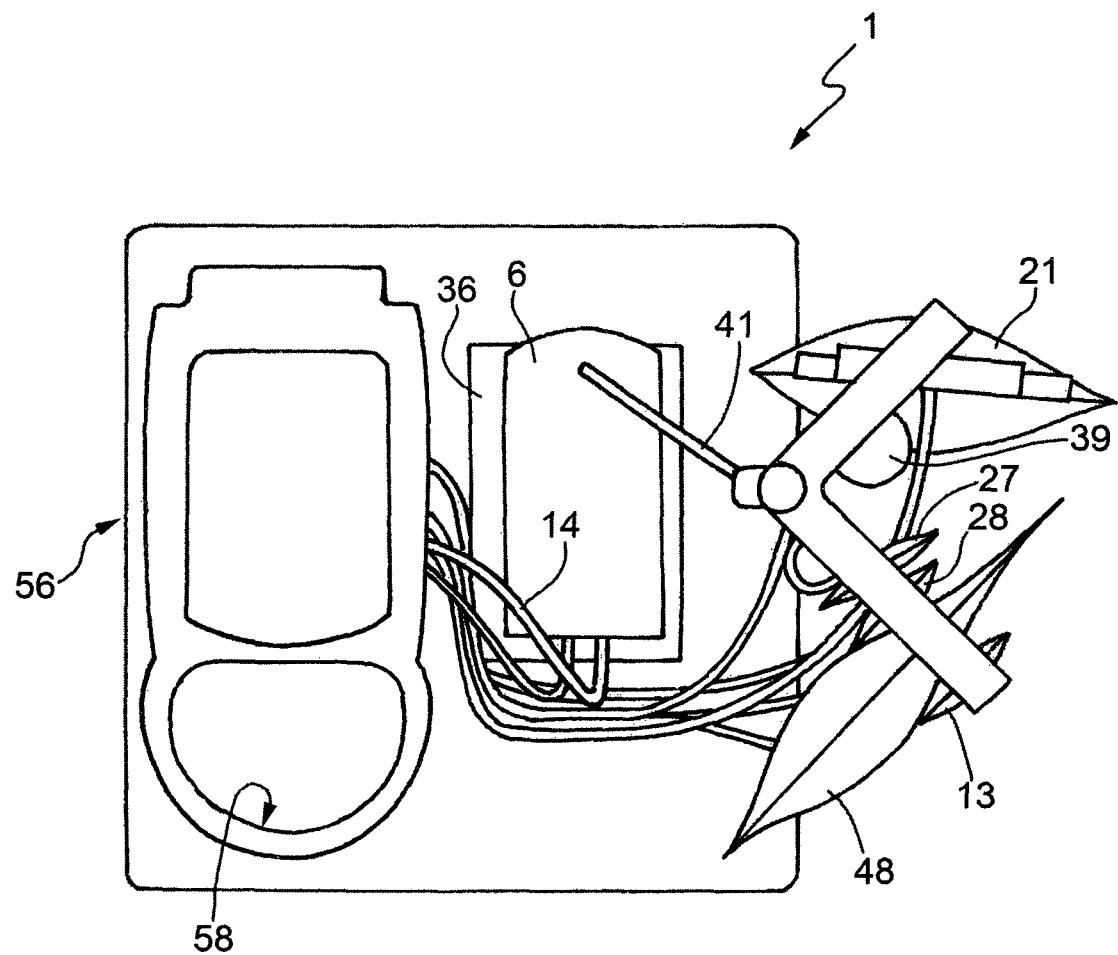
FIG. 5 is a diagrammatic top view, with details removed for clarity, of the apparatus in FIG. 1.
Figure 6:
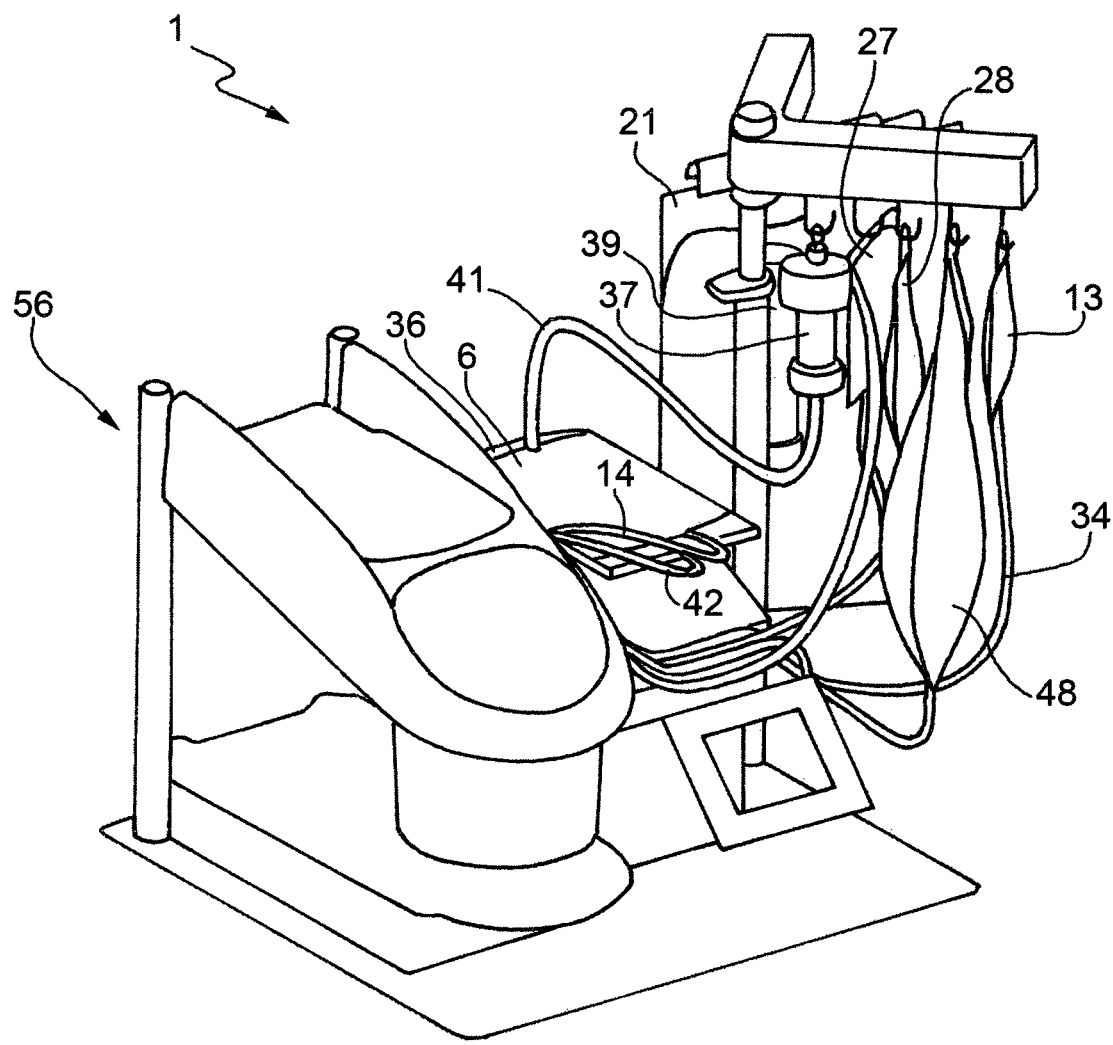
FIGS. 6 and 7 are side perspective views with details removed for clarity of the apparatus of FIG. 5.
Figure 7:
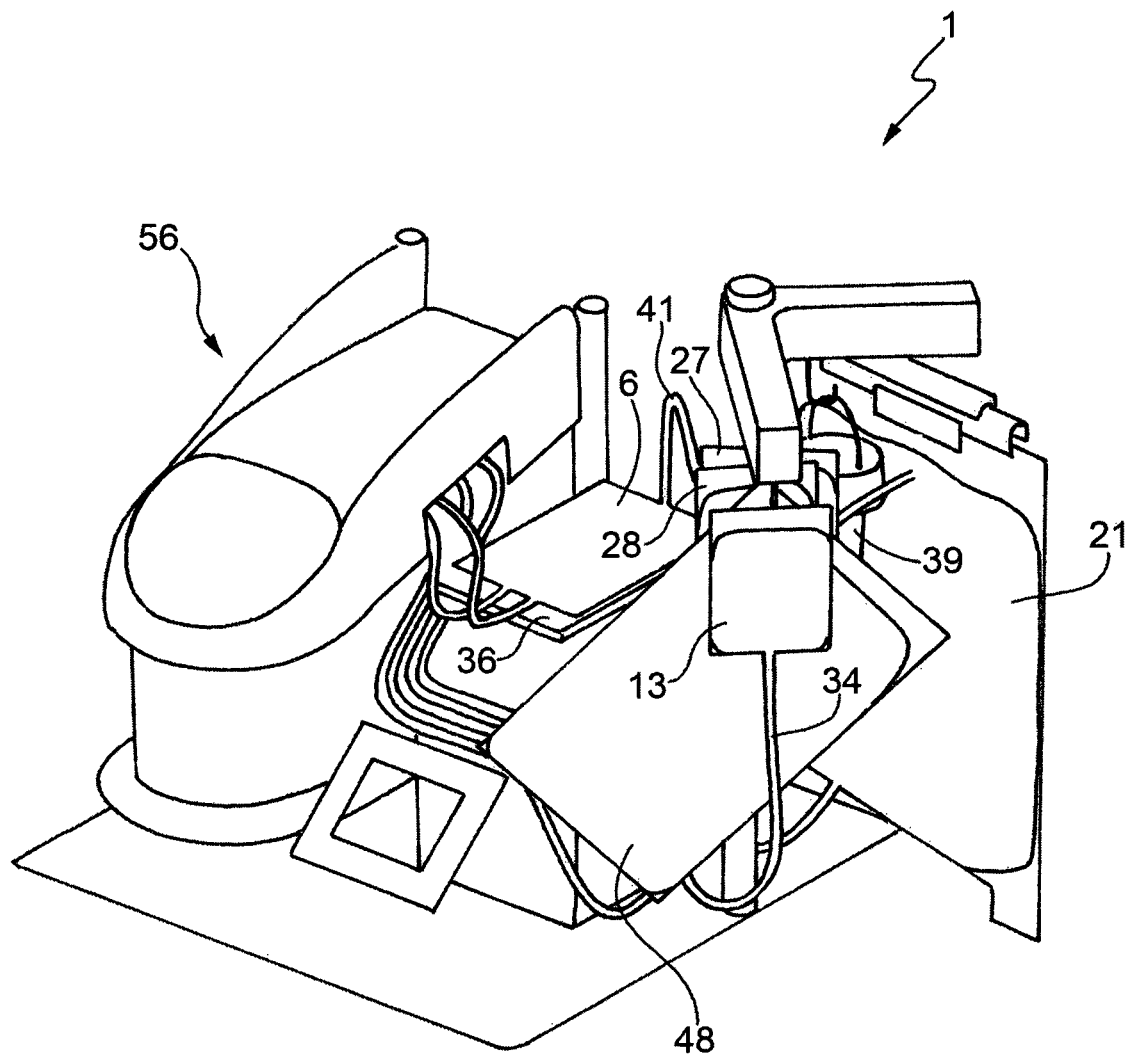

In FIG. 4, numerals 57 and 58 indicate a locking arm and a housing for separation bowl 24, respectively.

Above disclosed apparatus 1 has several advantages with respect to the state of the art. In particular, apparatus 1 allows to automate nearly all the operative steps to obtain the treated erythrocytes. Thereby, the time and possibility for the operator to make mistakes during the procedure are considerably reduced.

Apparatus 1 is also relatively simple, easy to carry and cost-effective. The use of apparatus 1 is further simplified and the safety is further improved in that apparatus 1 comprises a disposable kind of device 55.

In this connection, it should be noted that, according to advantageous embodiments, the apparatus comprises no more than three pumping means (in particular, between two and three) and at least four adjusting means (advantageously 5).

Furthermore, above disclosed apparatus 1 is extremely flexible allowing, among other things, to obtain treated erythrocytes with different concentrations of introduced compound and also with different haematocrits and final volumes.

Above disclosed apparatus 1 allows for a high degree of automation and control (without the need of a human control by an operator) of all the sequences of actions that allow to introduce at least one compound in the red blood cells.

In accordance with a second aspect of the present invention, there is provided a disposable kit for apparatus 1; the kit comprises device 55 as defined above or parts of device 55 to be assembled to obtain device 55.

In accordance with a third aspect of the present invention, device 56 is provided as defined above.

In accordance with a fourth aspect of the present invention, a method for introducing at least one compound (in particular, as defined above) within erythrocytes is provided. The method comprises a step of lysing, during which the erythrocytes are at least partially lysed being suspended in a hypotonic second solution (in particular, as defined above); and a first concentrating step, which is subsequent to the step of lysing and during which the at least partially lysed erythrocytes are concentrated by means of haemofiltration.

Advantageously, the method comprises a swelling step, which precedes the step of lysing and during which the erythrocytes are swollen by being suspended in a first hypotonic solution (in particular as defined above) so as to obtain a suspension; the first hypotonic solution has a greater concentration of solutes with respect to the second hypotonic solution.

According to some embodiments, the method is performed with the apparatus according to the first aspect of the present invention.

The method also comprises a combining step, which is simultaneous (or follows) the first concentrating step and during which the at least partially lysed erythrocytes are combined with the compound; a closing step, which follows the combining step and during which the at least partially lysed erythrocytes are closed so as to at least partially encapsulate the compound and obtain the treated erythrocytes; and a second concentrating step, which follows the closing step and during which the treated erythrocytes are concentrated.

The concentration of the treated erythrocytes after the closing step (and before the second concentrating step) is lower than the treated erythrocytes after the second concentrating step. More precisely, at the end of the closing step (and before the second concentrating step) the treated erythrocytes are in solution at a first concentration; at the end of the second concentrating step the treated erythrocytes are in solution at a second concentration higher than the first concentration.

During the second concentrating step, water is removed from the solution of treated erythrocytes. In other words, the solution of treated erythrocytes at the end of the closing step (and before the second concentrating step) has a higher water fraction with respect to the water fraction of the solution of treated erythrocytes at the end of the second concentrating step.

It should be noted that the present invention has, among other things, stemmed from the fact that surprisingly not all concentrations of treated erythrocytes lead to effective results. This problem was completely absent in the state of the art.

Advantageously, during the second concentrating step, the treated erythrocytes are concentrated by using a haemofilter.

According to some embodiments, the method comprises a third concentrating step, which follows the swelling step and precedes the lysing step and during which the content of water of the suspension is reduced, accordingly increasing the concentration of the erythrocytes in the suspension.

According to some embodiments, the third concentrating step is performed by using a separation step comprising a centrifuge unit (in particular as defined above).

Advantageously, during the closing step the at least partially lysed erythrocytes are placed in contact with the sealing solution (in particular, as defined above).

According to some embodiments, the method comprises a washing step, which follows the closing step (and possibly precedes the second concentrating step) and during which the treated erythrocytes are washed with a physiological solution. The washing step is adapted to remove the compound that has not entered the erythrocytes and other undesired substances (for example proteins or sealing solution).

In accordance with a fifth aspect of the present invention, a method for introducing at least one compound (in particular, as defined above) within erythrocytes is provided. The method comprises a step of lysing, during which the erythrocytes are at least partially lysed being suspended in a hypotonic second solution (in particular, as defined above); and a first concentrating step, which is subsequent to the step of lysing and during which the at least partially lysed erythrocytes are concentrated by means of haemofiltration.

Advantageously, the method comprises a swelling step, which precedes the step of lysing and during which the erythrocytes are swollen by being suspended in a first hypotonic solution (in particular as defined above) so as to obtain a suspension; the first hypotonic solution has a greater concentration of solutes with respect to the second hypotonic solution.

The method also comprises a combining step, which follows the concentrating step and during which the at least partially lysed erythrocytes are combined with the compound (or simultaneously with several compounds at the same time); a closing step, which follows the combining step and during which the at least partially lysed erythrocytes are closed so as to at least partially encapsulate the compound (or compounds) and obtain treated erythrocytes; and a second concentrating step, which follows the swelling step and precedes the lysing step and during which the water content of the suspension is reduced accordingly increasing the concentration of the erythrocytes in the suspension.

According to some embodiments, the method according to the fifth aspect of the present invention has one or more features of the method of the fourth aspect of the present invention (in this case, it should be noted that the second concentrating step of the fifth aspect corresponds to the third concentrating step of the fourth aspect and vice versa).

In accordance with a sixth aspect of the present invention, the use of an apparatus of the first aspect of the present invention is provided for the introduction of at least one compound within erythrocytes.

Advantageously, the compound is defined according to the above disclosure.

According to some embodiments, the use of the apparatus takes place according to the fourth and/or fifth aspect of the present invention.

In accordance with a specific aspect of the invention, an apparatus is provided for the introduction of at least one compound within the erythrocytes; apparatus 1 is similar (substantially identical) to that disclosed according to the first aspect of the present invention and differs therefrom because in addition or as an alternative to sensor 26, it has one or more of the following features. Apparatus 1 comprises reservoir 27 and reservoir 28 to contain the first and respectively the second solution. Channels 9 and 10 are connected to reservoir 27 and, respectively, to reservoir 28. Apparatus 1 comprises a weighing unit 51 to weigh the third and fourth reservoir 27, 28. Control unit 15 is adapted to control adjusting means 29 as a function of the weight of third reservoir 27 and adjusting means 30 as a function of the weight of the fourth reservoir 28. Apparatus 1 comprises a reservoir 21 to collect what has been separated from the erythrocytes by separating unit 4; a seventh reservoir 48 containing a third solution (in particular a physiological solution); a channel 47 connected to reservoir 48; and a channel 22 connected to reservoir 21. Channels 9 and 10 are connected to reservoir 27 and respectively to fourth reservoir 28. Apparatus 1 comprises a weighing unit 51 to weigh reservoirs 27 and 28, reservoir 21 and reservoir 13.

Control unit 15 is adapted to control pumping means 31 (and/or 40 and/or 49) as a function of the weight of reservoirs 13 (and/or 21 and/or 27 and/or 28 and/or 39 and/or 48).

In accordance with further aspects of the present invention the following is provided.

The solution (containing treated and concentrated erythrocytes, i.e. obtained after the second concentrating step) for use as a medicament.

The solution (containing treated and concentrated erythrocytes, i.e. obtained after the second concentrating step) for use in in vivo diagnosis.

The use of the solution (containing treated and concentrated erythrocytes, i.e. obtained after the second concentrating step) for the production of a medicament.

The use of the solution (containing treated and concentrated erythrocytes, i.e. obtained after the second concentrating step) for the production of a medicament.

A pharmaceutical composition comprising the solution (containing treated and concentrated erythrocytes—i.e. obtained after the second concentrating step).

Unless explicitly indicated otherwise, the content of the references (papers, texts, patent applications, etc.) cited in this text is herein integrally incorporated. In particular, the above mentioned references are herein incorporated by reference.

Further features of the present invention will result from the following disclosure of some embodiments of apparatus 1 given by mere way of non-limitative illustration.

Example 1

This example discloses operation tests of the device of FIG. 1. The method used hereinafter follows the indications of the description of the operation of apparatus 1 disclosed above with respect to the first aspect of the present invention.

Eight loading tests with dexamethasone sodium phosphate were performed (employing 500 mg for each procedure) in human red blood cells deriving from 50 ml of whole blood from healthy donors.

Figure 9:
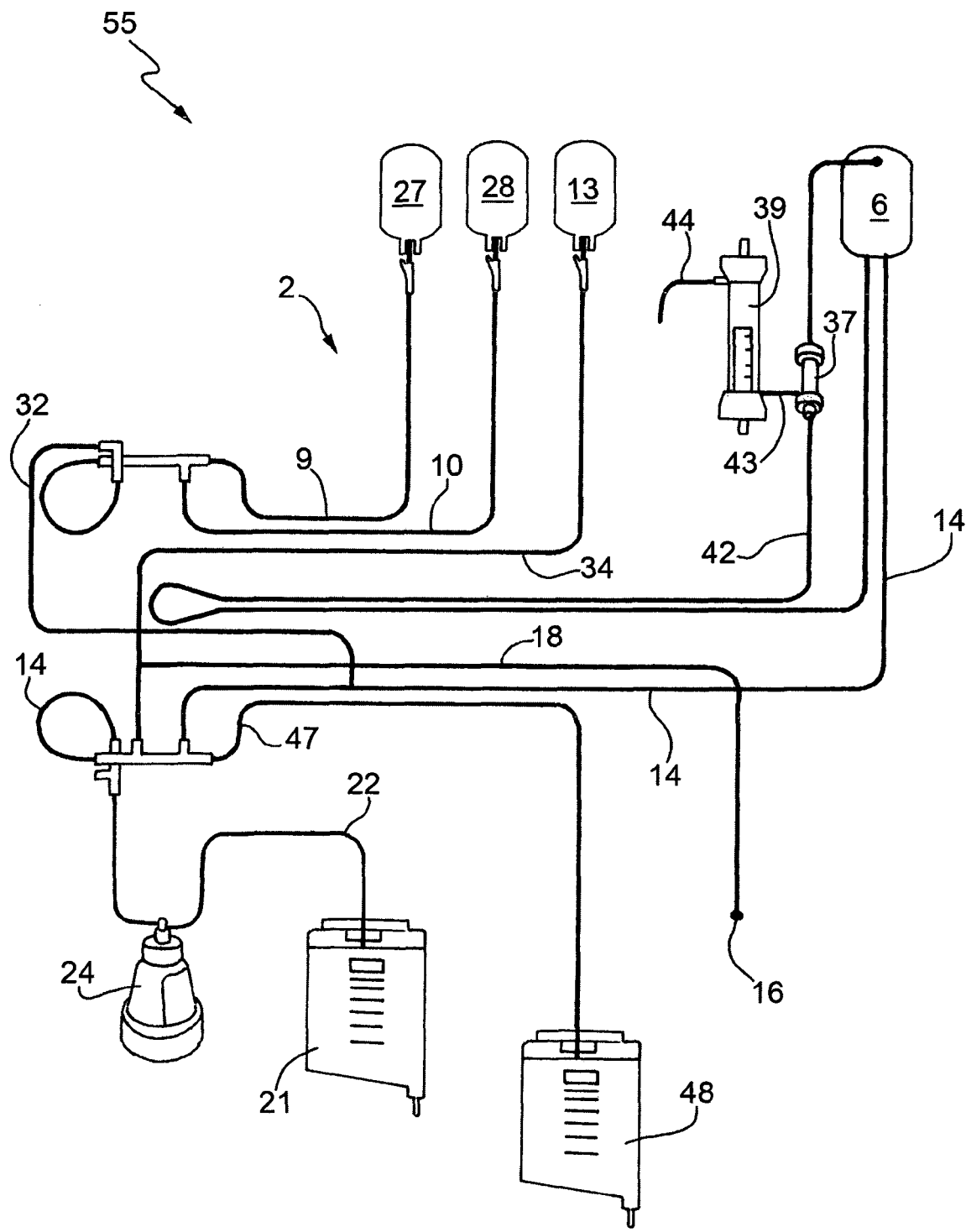
FIG. 9 diagrammatically shows a disposable device of the apparatus of FIG. 1.

The materials used for the tests are:
device of FIG. 4;
device of FIG. 9;
Hypotonic solution 1 (400 ml with an osmolality of 180 mOsm/Kg), Hypotonic solution 2 (200 ml with an osmolality of 120 mOsm/Kg);
Resealing hypertonic solution (PIGPA) (about 33 mM NaH$_2$PO$_4$; about 1.606 M KCl; about 0.194 M NaCl; about 0.1 M inosine; about 5 mM adenine; about 20 mM ATP; about 0.1 M glucose; about 0.1 M pyruvate; and about 4 mM MgCl$_2$) (7 ml at 2500-3800 mOsm/kg).
Dexamethasone sodium phosphate in aqueous solution 500 mg/20 ml (used completely)
Injectable grade physiological saline solution (aqueous solution of NaCl at 0.9% weight/volume) (2 L bags of which 1.8 L were used; 0.8 liters for the first washing and 1 L for the second washing)
50 ml whole blood from healthy donor anticoagulated with 10000 IU of sodic heparin Results The data obtained by the tests are shown in the following table, where the actual reproducibility of the results among different tests by standard deviation can be verified.

TABLE 1

| | | AVERAGE | STANDARD DEVIATION |
|---|---|---|---|
| Data on whole blood Pre-procedure | Volume of whole blood (ml) | 50.0 | 0.5 |
| | MCV (femtoliters) | 87.7 | 2.1 |
| | Haematocrit (%) | 40.0 | 4.6 |
| Data Post-procedure | MCV (femtoliters) | 80.1 | 3.9 |
| | Haematocrit (%) (without further concentration) | 10.0 | 1.7 |
| | Collection volume (without further concentration) (ml) | 83.9 | 3.9 |
| | Total dexamethasone sodium phosphate encapsulated within red blood cells (mg) | 12.30 | 3.0 |
| | Efficiency in the recovery of red blood cells with respect to initial number (%) | 43.1 | 10.3 |
| Data after further final concentration finale | Haematocrit (%) (after concentration) | 60.7 | 7.2 |
| | Collection volume (without further concentration) (ml) | 8.2 | 2.5 |

Table 1 shows the data of the whole pre-procedure blood, the data after the encapsulating procedure (including the loading of the drug in the red blood cells) and finally the effect of the increase of the haematocrit as a consequence of the final concentration by means of a further haemoconcentrating filter (or dialyser as shown in FIG. 2).

By effectiveness of the post-procedure step there is instead intended the percentage of the recovered blood cells with respect to the initial blood cells which started the process and correlates the net weight of the collection bag and the value of the haematocrit at the end of the process with respect to the volume and the value of the initial haematocrit of the blood used for the procedure.

The above data show that the object of the present invention allows to obtain erythrocytes loaded in an extremely effective and practical way and with optimum yields.

Example 2

Superparamagnetic Nanoparticles

Superparamagnetic nanoparticles are already available and used as contrast agents in Magnetic Resonance Imaging (MRI). However, once injected in the blood circulation by i.v. injection, the nanoparticles are rapidly covered by the plasmatic components of the blood, a process known as opsonisation that results pivotal in determining the faith of the nanoparticles making them easily recognisable for the major defence system of the body, i.e. the mononuclear phagocyte system. The encapsulation of superparamagnetic nanoparticles in human erythrocytes has therefore been obtained by the present apparatus, in order to avoid their rapid removal from the blood circulation and therefore obtain broader image time ranges in intravascular magnetic resonance applications (PCT/EP07/06349 Delivery of contrasting agents for magnetic resonance imaging). As an example, the loading of the contrast agent SHU555A has been performed by the above disclosed procedure and apparatus which are the object of the present patent, such as in FIG. 1. The concentration of SHU555A within the erythrocytes at the end of the procedure was determined following NMR measurements of the relaxivity (T1 and T2) of the samples. The encapsulation yield computed thereby determined SHU555A concentrations in the erythrocytes in the range of 1-2.1 mM Fe.

In order to verify whether the cells loaded with the magnetic nanoparticles by means of the apparatus disclosed in FIG. 1 maintained the properties of the native erythrocytes, measurements of some indicators of cell integrity were carried out. On the basis of these measurements, it was possible to establish that the procedure does not lead to significant modifications of the RBC properties such as mean corpuscular volume (MCV), mean corpuscular haemoglobin (MCH) and mean corpuscular haemoglobin concentration (MCHC) which result in the ranges for the previous example (dex 21 P). As a conclusion, the selected superparamagnetic nanoparticles were successfully encapsulated within the RBCs by means of the use of the apparatus shown in FIG. 1, therefore providing a product with the requirements for use in clinics to be used for diagnostic purposes in MRI (magnetic resonance imaging).

Example 3

Contrast Agent Indocyanine Green (ICG)

Another application of the innovative technique relating to the transport of exogenous molecules into red blood cells is represented by the encapsulation of contrast agents to be used in fluoroangiography or with other optical and/or fluorescence detection methods. As an example, results are shown of the encapsulation of the contrast agent indocyanine green (ICG) obtained with the apparatus as shown in FIG. 2. This is proposed as a new strategy for diagnostic and therapeutic purposes for the display and/or the photocoagulation of new vessels of the choroid in degenerative and vascular diseases of the retina.

ICG is an infrared (IR) contrast agent containing tricarbocyanine and approved by the FDA for diagnostic use to display the vascularisation of the retina and for photodynamic therapy. Its use as a contrast agent takes advantage of the fact that most biological molecules neither absorb nor emit in the region near IR, thus leading to an interference free fluorescence. The actual use of ICG as a fluorescent marker and photostabilising agent is however limited by several factors: Instability in water, degradation due to light and heat, short half-life in the blood circulation (about 2-4 minutes) and fast hepatobiliary clearance due to binding to plasma proteins. Furthermore, the ICG molecules can diffuse through the vessels and the diffusion process could influence the angiographic semiology. The delivery of ICG in the vascular compartment by using erythrocytes as carriers allows to overcome such limitations. Thereby, once the molecule is within the RBCs, it is on one side protected from inactivation by endogenous factors and, on the other side, its encapsulation in autologous RBCs implies a protection of the organism against the toxic effects of the agent itself (nausea, vomit, rash, hypotensive shock, etc.). In light of this and in order to significantly improve the features of coroidal angiography and of laser photocoagulation, the apparatus in the version shown in FIG. 2 was used, so as to load ICG into autologous human erythrocytes. After the red blood cells were loaded, they were concentrated again by using a second haemofilter so as to obtain the same amount of ICG in a reduced volume of erythrocyte suspension having a higher haematocrit and therefore a higher ICG concentration.

When the ICG encapsulating procedure was completed using the apparatus as defined in FIG. 2, thus with a final step of further erythrocyte concentration, 6 ml of ICG containing RBC (0.3 μmoli/ml RBC) were obtained with a 44% haematocrit which can be further increased up to 60% haematocrit by extending the concentrating step.

Example 4

Targeting of Erythrocytes with Encapsulated Pharmacologically Active Substances and/or Encapsulated Substances for Diagnostic Use The targeting to macrophages of erythrocytes containing drugs and/or contrast means can be achieved by the apparatus shown in the figure following a procedure similar to that used in example 1. When fludarabine was used as an encapsulating agent, a final concentration of 0.8 mM was obtained. The erythrocytes treated in this way were recognised by autologous IgGs in percentages over 80% the total number of processed cells.

Example 5

Figure 10:
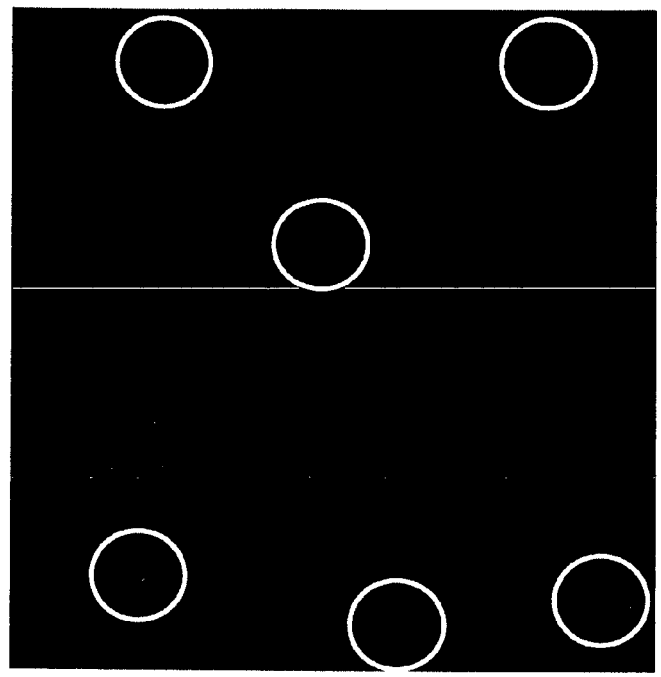
FIG. 10 is a fluoroangiographic image obtained by using an infusion of erythrocytes loaded with Indocyanine Green with a haematocrit of 6.4%.

A first solution of erythrocytes loaded with Indocyanine Green was obtained. This solution (which was not concentrated after loading the indocyanine in the erythrocytes) had a haematocrit of 6.4% and was injected in a patient. FIG. 10 is a fluoroangiographic image of the patient treated in this way.

Figure 11:
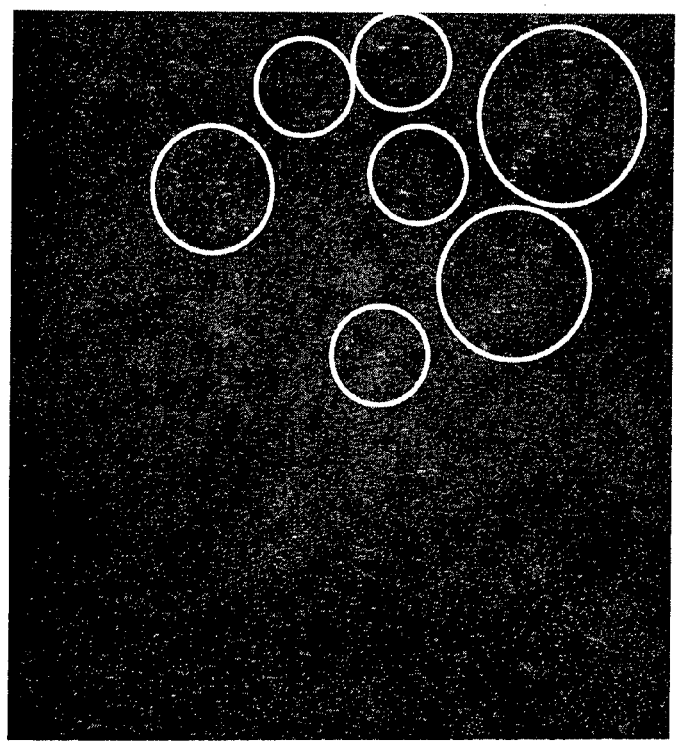
FIG. 11 is a fluoroangiographic image obtained by using an infusion of erythrocytes loaded with Indocyanine Green with a haematocrit of 54%.

A second solution of erythrocytes loaded with Indocyanine Green was obtained. This solution (which was not concentrated after loading the indocyanine in the erythrocytes) had a haematocrit of 54% and was injected in a patient. FIG. 11 is a fluoroangiographic image of the patient treated in this way.

From the comparison of the two images it is clear that surprisingly, where the diluted solution (FIG. 10) does not allow a diagnosis, the concentrated solution (FIG. 11) allows an easy diagnosis.

In this connection, it should be noted that, before the present invention, it was not foreseeable that the result of an increased concentration would be such a clear result. In particular, it is absolutely surprising that the loaded erythrocytes were not dispersed in the organism, but instead moved together and therefore allowed to obtain an extremely clear image.

The invention claimed is:

1. An apparatus for introducing at least one compound within erythrocytes; the apparatus (1) comprises a system (2) of connection channels, which includes a first and a second channel (9, 10); an introducing unit (3) for inserting a sample containing the erythrocytes within the apparatus (1); a separating unit (4) for separating the different components of the sample from one another; a combining unit (5), which comprises a first reservoir (6) and in the area of which the erythrocytes and the compound are combined together so as to obtain treated erythrocytes; an inlet (7) for inserting the compound in the first reservoir (6); a feeding unit (8), for feeding a first solution through the first channel (9) and feeding a second solution through the second channel (10); a concentrating unit (11) for concentrating the content of the first reservoir (6); and a collecting unit (12), which comprises a second reservoir (13) for collecting treated erythrocytes;

the concentrating unit (11) comprising a filter (37) for at least partially separating the erythrocytes from a liquid so as to increase the concentration of the erythrocytes; an aspirator (38), which is controlled by a control unit (15) and is adapted to suck at least part of the liquid through the filter (37);

the system (2) of channels connecting the introducing unit (3), the separating unit (4), the combining unit (5), the feeding unit (8), the concentrating unit (11) and the collecting unit (12);

the apparatus (1) further comprising the control unit (15); and first pumping means (49), which are actuatable by the control unit (15) and are designed to move fluids at least between the introducing unit (3), the separating unit (4), the combining unit (5) and the collecting unit (12);

the feeding unit (8) comprises a first adjusting device (29), which is actuatable by the control unit (15) and is arranged along the first channel (9) to regulate the flow along the first channel (9); and a second adjusting device (30), which is actuatable by the control unit (15) and is arranged along the second channel (10) to regulate the flow along the second channel (10);

the collecting unit (12) comprises a third adjusting device (33), which is actuatable by the control unit (15) and is adapted to adjust the flow towards the second reservoir (13);

the apparatus comprises an air sensor (26) for identifying the presence of air in the system (2) of channels between the introducing unit (3) and the separating unit (4).

2. The apparatus according to claim 1, wherein the feeding unit (8) comprises second pumping means (31), which are actuatable by the control unit (15) and are designed to move the first and the second solution towards the combining unit (5).

3. The apparatus according to claim 1, wherein the combining unit (5) comprises a mixing device (35) controllable by the control unit (15) to move the first reservoir (6) so as to mix the content thereof; and at least one heating element controllable by the control unit (15) to heat the content of the first reservoir (6).

4. The apparatus according to claim 1, comprising a third reservoir (27) and a fourth reservoir (28) for containing the first and respectively the second solution; the first and the second channel (9, 10) being connected to the third reservoir (27) and to the fourth reservoir (28), respectively; the apparatus (1) comprising a weighing unit (51) for weighing the third and the fourth reservoir (27, 28); the control unit (15) is adapted to control the first adjusting device (29) as a function of the weight of the third reservoir (27) and the second adjusting device (30) as a function of the weight of the fourth reservoir (28).

5. The apparatus according to claim 1, comprising a further feeding unit (45), which is designed to feed a third solution (in particular a physiological solution) along a third channel (47) of the system (2) of channels and comprises a fourth adjusting device (46), which is actuatable by the control unit (15) and is arranged along the third channel (47) for regulating the flow along the third channel (47).

6. The apparatus according to claim 1, wherein the system (2) of channels comprises a connection channel (14) between the combining unit (5) and the separating unit (4); said first pumping means (49) being arranged along the connection channel (14); the introducing unit (3), the collecting unit (12), the feeding unit (8) and the further feeding unit (45) being connected to the connection channel (14) between the first pumping means (49) and the combining unit (5).

7. The apparatus according to claim 6, comprising a fifth adjusting device (50), which is actuatable by the control unit (15) and is arranged along said connection channel (14) between the feeding unit (8) and the separating unit (4) and between the introducing unit (3), the collecting unit (12) and the further feeding unit (45) on one side and the combining unit (5) on the other side.

8. The apparatus according to claim 1, wherein the introducing unit (3) comprises a sixth adjusting device (19), which is actuatable by the control unit (15) and is adapted to regulate the flow from the introducing unit (3).

9. The apparatus according to claim 1, wherein the concentrating unit (11) comprises a fifth reservoir (39) for collecting the liquid that has passed through the filter (37); and third pumping means (40) for conveying the content of the first reservoir (6) in contact with the filter (37); the apparatus (1) comprising a weighing unit (51) for weighing the fifth reservoir (39); the control unit (15) is adapted to control the aspirator (38) as a function of the weight of the fifth reservoir (39) detected by the weighing unit (51).

10. The apparatus according to claim 1, wherein the separating unit (4) comprises a centrifuge assembly (20) for separating the erythrocytes and/or the treated erythrocytes from the other components.

11. The apparatus according to claim 1, comprising a third reservoir (27) and a fourth reservoir (28) for containing the first and respectively the second solution; a sixth reservoir (21) for collecting what has been separated from the erythrocytes by the separating unit (4); a seventh reservoir (48) containing a third solution (in particular a physiological solution); a third channel (47) connected to the seventh reservoir (48); and a fourth channel (22) connected to the sixth reservoir (21); the first and the second channel (9, 10) being connected to the third reservoir (27) and respectively to the fourth reservoir (28); the apparatus (1) comprising a weighing unit (51) for weighing the third, the fourth reservoir (27, 28), the sixth reservoir (21) and the second reservoir (13); the control unit (15) is adapted to control the pumping means (31; 40; 49) as a function of the weight of the reservoirs (13; 21; 27; 28; 39; 48).

12. The apparatus according to claim 1, comprising a reusable device (56), which comprises pumping means, the first, second and third adjusting devices, the control unit (15), the air sensor (26), the weighing device (51) and the aspirator (38); and a disposable device (55) which comprises the system (2) of channels, and the first and second reservoirs.

13. A reusable device according to claim 12.

14. The apparatus according to claim 1, wherein the combining unit (5) comprises a mixing device (35) controllable by the control unit (15) to move the first reservoir (6) so as to mix the content thereof; and at least one weighing device for weighing the content of the first reservoir (6).

15. A disposable kit for the apparatus (1) according to claim 1; the kit comprises the system (2) of channels and the reservoirs connected to the system (2) of channels of the apparatus (1); at least one of the channels (14) of the system (2) of channels has at least one segment with a hardness lower than 70 Shore A; said segment being adapted to be arranged at sensor (26).

16. The kit according to claim 15, comprising at least one filter (37) for the concentrating unit (11), a separating bowl (24) for a centrifuge assembly (20) for the separating unit (4), a sixth reservoir (21) for collecting what has been separated from the erythrocytes by the separating unit (4) and a seventh reservoir (48) for containing the third solution (in particular a physiological solution).

17. Use of an apparatus according to claim 1 for introducing at least one compound within erythrocytes; the compound is selected from the group consisting of:
- active pharmacological agents, peptides, proteins, hormones, dexamethasone sodium phosphate and betamethasone sodium phosphate, glutathione, toxins, single stranded or double stranded oligonucleotides, nucleotide analogues, nanoparticles with a diameter up to 500 nm, fluorescent agents, other agents detectable by optical, echographic or magnetic resonance apparatuses, other contrast agents that are usable as diagnostic means;
- the use comprising a lysis step, during which the erythrocytes are at least partially lysed;
- a concentration step, during which the at least partially lysed erythrocytes are concentrated by means of the concentrating unit;
- a combination step, wherein the compound is combined with the concentrated and at least partially lysed erythrocytes.

18. The use according to claim 17, wherein during the lysis step the erythrocytes are at least partially lysed in the area of the first reservoir by means of said second solution;
- during the concentration step, a liquid, wherein the at least partially lysed erythrocytes are suspended, is sucked through the filter so as to separate it from the at least partially lysed erythrocytes;
- during the combination step, a seal solution is contacted with the at least partially lysed and concentrated erythrocytes so as to reseal the at least partially lysed and concentrated erythrocytes and at least partially encapsulate the compound in the at least partially encapsulated in the lysed and concentrated erythrocytes.

19. The use according to claim 18, and comprising a swelling step, during which the erythrocytes are at least partially swollen by means of said second solution in the area of the first reservoir.

20. The apparatus according to claim 1, and comprising a sixth reservoir for collecting what has been separated from erythrocytes from said separating unit and a weighing device for detecting the weight of the sixth reservoir.

21. The apparatus according to claim 1, wherein the filter is selected in the group consisting of: haemofilter and dialysis filter.

* * * * *